United States Patent [19]

Yager et al.

[11] Patent Number: 5,094,819
[45] Date of Patent: Mar. 10, 1992

[54] FLUORESCENCE-BASED OPTICAL SENSOR AND METHOD FOR DETECTION OF LIPID-SOLUBLE ANALYTES

[75] Inventors: Paul Yager, Seattle, Wash.; Richard B. Thompson, Baltimore, Md.; Sabina Merlo, Seattle, Wash.

[73] Assignee: Washington Research Foundation, Seattle, Wash.

[21] Appl. No.: 367,508

[22] Filed: Jun. 16, 1989

[51] Int. Cl.⁵ .......................................... G01N 21/64
[52] U.S. Cl. .................... 422/82.07; 128/634; 250/227.14; 250/459.1; 250/483.1; 422/56; 422/57; 422/58; 422/82.02; 422/82.11; 436/126; 436/132; 436/169; 436/172; 436/178
[58] Field of Search ............. 436/126, 131, 132, 139, 436/140, 141, 169, 170, 172, 178; 422/56, 57, 58, 82.06, 82.07, 82.08, 82.11; 250/459.1, 461.2, 227.14, 483.1; 128/634

[56] References Cited

U.S. PATENT DOCUMENTS

| | | |
|---|---|---|
| 4,255,053 | 3/1981 | Lubbers et al. .................. 356/318 |
| 4,306,877 | 12/1981 | Lubbers ............................ 422/91 X |
| 4,682,895 | 7/1987 | Costello ........................ 422/82.06 X |
| 4,929,561 | 5/1990 | Hirschfeld .................... 422/82.06 X |

FOREIGN PATENT DOCUMENTS 2132348  7/1984  United Kingdom .

*Primary Examiner*—Robert J. Hill, Jr.
*Attorney, Agent, or Firm*—Christensen, O'Connor Johnson & Kindness

[57] ABSTRACT

A sensor, probe, system and method for detecting the presence of or concentration of lipid-soluble analytes such as anesthetics, which involve the use of fluorophore-containing lipid layers or similar amphiphilic structures as the sensor. The lipid layer is constituted such that it has a phase transition temperature equal to or close to the temperature at which the measurement of the analyte is conducted. Partitioning of a suitable analyte into the lipid layer results in a phase change which is then reflected in a change in a fluorescence characteristic, such as a shift in the wavelength of maximum intensity of fluorescence, of the fluorophore, in proportion to the amount of analyte.

30 Claims, 9 Drawing Sheets

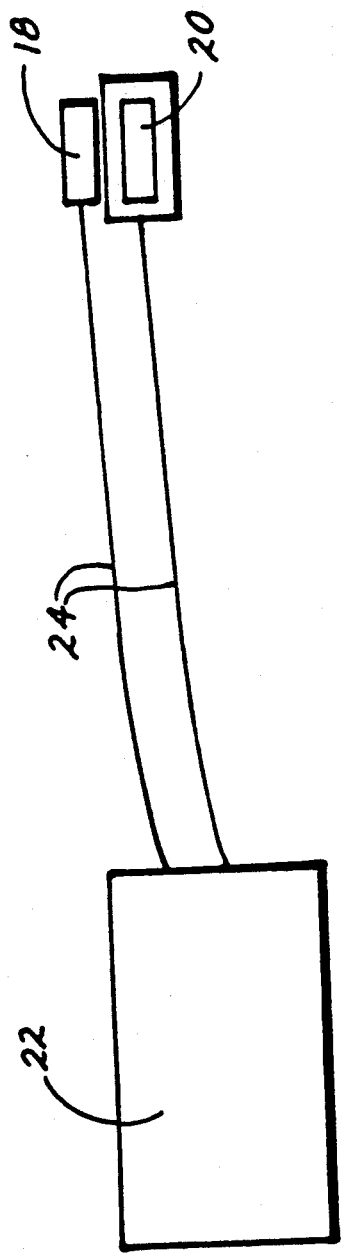

FLUORESCENCE-BASED OPTICAL SENSOR AND METHOD FOR DETECTION OF LIPID-SOLUBLE ANALYTES

FIELD OF THE INVENTION

The present invention is directed to a fluorescence-based optical sensor, probe, system and methods based thereon for determining the presence and/or concentration of lipid-soluble analytes, such as general anesthetics.

BACKGROUND OF THE INVENTION

Determination of the concentration of an anesthetic in a patient has been of great interest in research and in clinical practice. At present, there are no methods in use that measure the levels of anesthetics in target tissues in real time. As the target tissues take up anesthetics from blood at widely differing rates that depend on the precise condition of the patient, methods that determine the concentration of anesthetics in any one body compartment, such as the lungs or blood, do not reliably reflect the depth of anesthesia of the patient as a whole.

The most reliable method of measuring anesthetics currently in use in surgical procedures is to extract large volumes of blood from the patient for gas chromatography. In the case of infants, so much blood must be removed that the determinations are dangerous to the health of the patient. Moreover, this type of measurement involves significant time delays since the blood sample must be sent to a laboratory for measurement. Obtaining results can take hours or days. Such time delays are not compatible with a surgical procedure on a patient.

The levels of inhalation anesthetics can be monitored with substantially less trauma by measuring the content of such volatiles in the exhaled air by a variety of methods. One device monitors exhaled and inhaled anesthetic levels by the increase in mass of an oil droplet on a piezoelectric crystal that occurs as the anesthetic partitions into the droplet.

The following article is of relevance to the detection of anesthetics in patients: Wolfbeis, O.S., et al. "Fiber Optical Fluorosensor for Determination of Halothane and/or Oxygen," *Anal. Chem.*, 57:2556-2561 (1985). Wolfbeis et al. report the development of a method of monitoring the concentration of halothane in air using a silicone rubber membrane impregnated with a fluorophore that is quenched by this particular type of anesthetic.

Commercially available devices (such as the Datex monitor) monitor certain inhalation anesthetics in air by the intensity of their characteristic infrared absorption spectra.

Other research groups have developed fiber-optic biosensors for analytes not necessarily limited to anesthetics. Reports of this nature, which appear to be relevant to the present invention, are the following:

(1) Krull, U. J., et al. (Krull I), "Towards a Fluorescent Chemoreception Lipid Membrane-Based Optrode," *Talanta* 35:129-137 (1988).

(2) Krull, U. J., et al. (Krull II), "Supported Chemoreceptive Lipid Membrane Transduction by Fluorescence Modulation: the Basis of an Intrinsic Fibre Optic Biosensor," *Analyst*, 111:259-261 (1986).

(3) Lakowicz, J. R. et al., "Synthesis and Characterization of a Fluorescence Probe of the Phase Transition and Dynamic Properties of Membranes," *Biochemistry*, 22:5714-5722 (1983).

Krull I and II report progress in development of fiber-optic based sensors employing fluorescent detection of molecules that partition into lipid layers on the fibers. In these reports, the responses of fluorophores such as 1-anilinonaphthalene-8-sulphonate in "dry" lipid monolayers on optical waveguides to the concentration of gaseous chloroform, hexane, and N, N-dimethyl-aniline are measured. No response to changes in concentration of chloroform and hexane were seen when the fluorophore was embedded in fatty acid monolayers, and only transient changes were observed when the fluorophore was incorporated in phosphatidylcholine/cholesterol monolayers.

The method of determining the concentration of an analyte of the present invention is based on a change in a fluorescence characteristic of a fluorophore embedded in a lipid layer caused by a phase change of the lipid layer. The phase change of the lipid layer is a result of, and proportional to, partitioning of an analyte (such as an anesthetic) into the lipid layer. As opposed to the present invention, Krull I and II do not involve a phase change of the lipid layer as a result of partitioning of the analyte into the lipid layer. Krull I and II involve detection of analytes based on changes in fluorescence intensity of a fluorophore due to changes in fluidity and packing of the lipid layer. Thus, while the method of Krull I and II involves a change within a single phase of a lipid layer induced by an analyte, the present method involves a change between phases induced by the analyte.

Lakowicz et al. describes the synthesis and characterization of a new fluorescence probe for biological membranes. The novel fluorescent probe, 6-palmitoyl-2-[[2-(trimethyl-ammonio)ethyl] methylamino] naphthalene chloride (also known as Patman), consists of a trimethyl ammonium head, a fluorescent naphthalene body, and a hydrophobic palmitoyl tail. Because of its structure, Patman orients itself in a phospholipid membrane with its tail embedded in the core of the lipid bilayer and its head associated with the hydrophilic surface. Patman is described as being a useful probe for studying dynamic properties (fluidity) of biological membranes. Both fluorescence lifetime and emission frequency of the excited state of Patman reflect fluidity changes in the lipid bilayer. Lakowicz et al. does not suggest the use of Patman in a lipid layer which is subject to phase changes due to the presence of an analyte.

In summary, while the above-described references are directed to detection of analytes based on fluorescence measurements and changes, in some cases involving a lipid layer, none of them involve analyte detection or quantitation based on a change in a fluorescence characteristic of a fluorophore based on a phase change in a lipid layer. None of them discuss immobilization of the lipid layer using a hydrogel, another (optional) feature of the present invention which is described hereinbelow. Moreover, none of these references describe or suggest the use of impermeable or semipermeable membranes as barrier layers between the lipid layers and the medium containing the analyte, additional possible features of the present invention which will be summarized and described in detail hereinbelow.

The patent literature related to the present invention is represented by the following patents:

1. Wolfbeis et al., U.S. Pat. No. 4,568,518
2. Marsoner et al., U.S. Pat. No. 4,657,736

3. Krull et al., U.S. Pat. No. 4,637,861
4. Krull et al., U.S. Pat. No. 4,661,235
5. Miller et al., U.S. Pat. No. 4,666,672

Wolfbeis et al., in U.S. Pat. No. 4,568,518, disclose a sensor element for fluorescence optical measurements, comprising a carrier membrane with fluorescent indicator material immobilized thereon. A network structure containing the indicator material is integrated into a carrier membrane. The carrier membrane is made of cellulose while the network structure permeating the carrier is composed of material containing amino groups, such as hexamethylene diamine or polyethyleneimine and the indicator 1-acetoxypyrene-3,6,8-trisulphochloride.

Marsoner et al., in U.S. Pat. No. 4,657,736, disclose an oxygen sensor element that, when placed in contact with a sample containing oxygen, is capable of indicating the concentration of oxygen in the sample. The sensor element is composed of cured silicone polymer that is permeable to oxygen and a chemically modified oxygen-sensitive fluorescent indicator that is homogeneously embedded in the cured silicone polymer. The fluorescent indicator includes compounds such as polycyclic aromatic hydrocarbons, homocyclic aromatic hydrocarbons, and heterocyclic aromatic hydrocarbons. Usually these fluorescent indicators display fluorescent decay times greater than five nanoseconds. Contact of oxygen with the fluorescent material embedded in the silicone matrix causes quenching of the fluorophore, thereby indicating the oxygen concentration.

Krull et al., in U.S. Pat. No. 4,637,861, disclose an ion permeable lipid membrane-based device capable of detecting a particular chemical species in an aqueous electrolytic solution. The device produces a signal based on increased ion permeability of the membrane when it is exposed to the chemical species to be detected and when an electrical potential is applied across it. Phospholipid molecules are covalently linked to a substrate to produce the lipid membrane of this device.

Krull et al., in U.S. Pat. No. 4,661,235, disclose a lipid based membrane transducer. According to this invention, a lipid bilayer composed of phospholipids and cholesterol is used as a barrier or modulator of ion flow through the membrane. The particular membrane chosen is one that is electrically neutral toward the test solution containing the ion to be measured. A potential is applied across the membrane and conductivity of the ion through the membrane is measured. In this way, the target ionic species can be quantitatively determined.

Miller et al., in U.S. Pat. No. 4,666,672, disclose an "optrode" for sensing hydrocarbons. According to these inventors, a two-component system is employed in the fluorometric detection of halogenated hydrocarbons. A fiber-optic element is used to illuminate a column of pyridine trapped in a capillary tube coaxially attached to one end of the fiber optic. The other component consists of a strongly alkaline solution in contact with the column of pyridine and capped at the other end with a semipermeable membrane. The semipermeable membrane is preferentially permeable to halogenated hydrocarbons and impermeable to water and pyridine. As halogenated hydrocarbon diffuses through the membrane and into the column of pyridine, fluorescent reaction products are formed. Light propagated by the fiber optic from a light source then excites the fluorescent species and fluorescent emission is conducted back through the fiber-optic cable to a detector. The intensity of the fluorescence gives a measurement of the concentration of the halogenated hydrocarbons.

In summary, none of the above-described patents disclose a sensor based on a lipid layer with a fluorophore embedded therein in which a fluorescence characteristic of the fluorophore varies in response to a phase change in the lipid layer caused by an analyte dissolving therein.

More generally, in spite of the above-described background art, a need has continued to exist for new and improved ways of measuring the concentrations of lipid-soluble analytes, such as anesthetics in tissues of patients and animals, in real time.

SUMMARY OF THE INVENTION

In a broad sense, the present invention relates to a sensor for determining the presence or concentration of a lipid-soluble analyte in a medium containing the analyte, and to a method of determining the presence of or concentration of an analyte based on such sensors. Representative lipid-soluble analytes include anesthetics, drugs, alcohols, pollutants and other organic chemicals used in industrial processes. The medium may be either a liquid, a gas or a semisolid, such as a gel or biological tissue. If a solid medium is utilized, the analyte may diffuse from the solid, or the solid may be particulated or may be dissolved in a suitable liquid for analysis. The sensor comprises a fluorophore contained in a lipid layer, wherein a fluorescence characteristic of the fluorophore varies in response to the analyte partitioning into the lipid layer. The lipid layer is selected so as to have a phase transition temperature equal to the temperature of the medium to be analyzed, or within one-half the phase transition temperature range of the lipid layer. As the analyte becomes associated with or dissolves into the lipid layer, the phase transition temperature of the lipid layer varies accordingly.

The sensor may be connected to an optical transmission means, such as an optical waveguide (e.g., an optical fiber), capable of transmitting fluorescence excitation radiation from a source to the fluorophore and capable of transmitting fluorescence emission radiation from the fluorophore to a detector. When so connected, the sensor plus the optical transmission means is collectively referred to as a probe. When the optical transmission means is an optical fiber, the probe is referred to as an optrode. When the probe is connected to a fluorescence excitation source and/or a fluorescence emission detector, along with other electronic devices such as data storing or computing means, the assembly is collectively referred to as a system. The present invention is directed to sensors, probes and systems, and methods of analyzing for the presence or amount of an analyte based thereon.

It is also possible for the sensor to be directly irradiated with fluorescence excitation radiation from a source without optical transmission means, e.g., in a cuvette in a fluorometer. Measurement of emitted fluorescence could likewise be accomplished without optical transmission means. Thus, the sensor need only be brought into contact with a medium containing or suspected of containing an analyte, with some provision for fluorescently exciting the fluorophore and measuring a change in fluorescence emitted by the fluorophore.

The apparatus may also include a reference sensor having the same composition of lipid layer and fluorophore as the sensor, except that in the reference sensor, the lipid layer is separated from the medium containing the analyte by a thermally conductive barrier membrane that is impermeable to the analyte, lipid molecules and fluorophore. The reference sensor is held at the same temperature as the sensor, making possible a direct determination of the analyte concentration.

Also, optionally, the sensor may include a semipermeable membrane that separates the lipid layer from the medium. The semipermeable membrane should be permeable to the analyte, but impermeable to the fluorophore, lipid molecules making up the lipid layer, and/or potentially interfering analytes. This can prevent fluorophore or lipid leakage from the lipid layer.

BRIEF DESCRIPTION OF THE DRAWINGS

The present invention will become better understood by reference to the following drawings, wherein:

FIG. 2 shows a block diagram of a general embodiment of the invention. The system is made up of a sensor (18), a reference sensor (20), optics and electronics (22) for fluorescence excitation and comparison of emission from the sensor and the reference sensor, and optical transmission means (24).

FIG. 3A shows spheroidal lipid bilayers (liposomes) (26) that contain fluorophore molecules (not shown). The liposomes are immobilized in a hydrogel (28).

FIG. 3B shows multilayered lipid molecules having hydrophobic moieties (30) and hydrophilic moieties (32) and containing in the hydrophobic moieties fluorophore molecules (34). The multilayers are held near substrate (36) by association with hydrophobic groups (38) covalently linked to the substrate.

FIG. 3C shows a lipid monolayer (40) containing a fluorophore (42) and held near a substrate (44) by association with hydrophobic groups (46).

FIG. 3D shows a lipid monolayer (48) held near a substrate (50) by association with hydrophobic groups (52). A fluorophore (54) is covalently linked to the substrate by linker moieties (56).

FIG. 3E shows a lipid layer (58) and fluorophores (60) each covalently linked to a substrate (62) by linker moieties (64).

DETAILED DESCRIPTION OF THE INVENTION AND ITS PREFERRED EMBODIMENTS

Figure 1B:
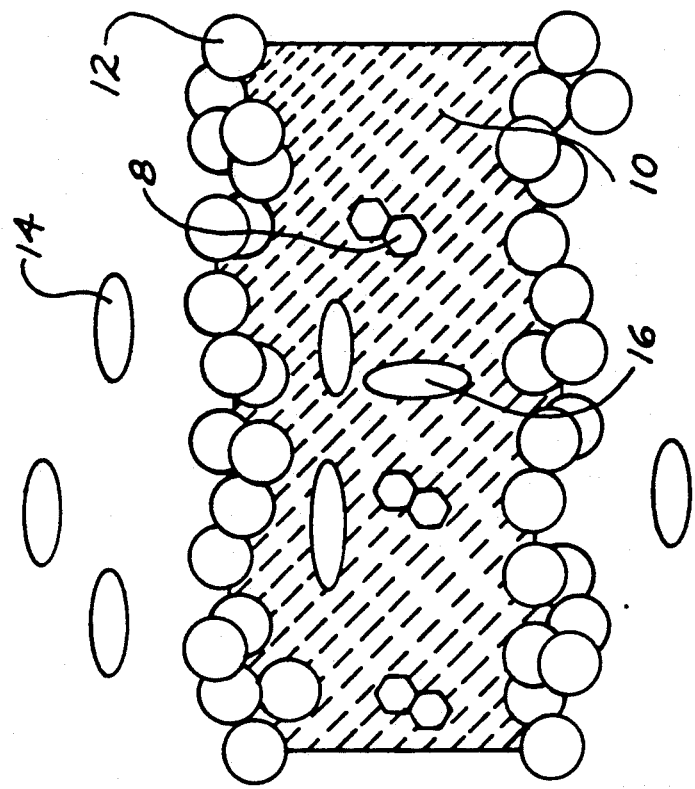
FIG. 1B depicts a fluorophore (8) contained in a liquid lipid bilayer made up of disordered hydrophobic moieties (10) and hydrophilic head groups (12). An analyte in a medium (14) has, in part, dissolved in the medium (16) to cause the lipid bilayer to undergo a solid to liquid phase change.
Figure 1A:
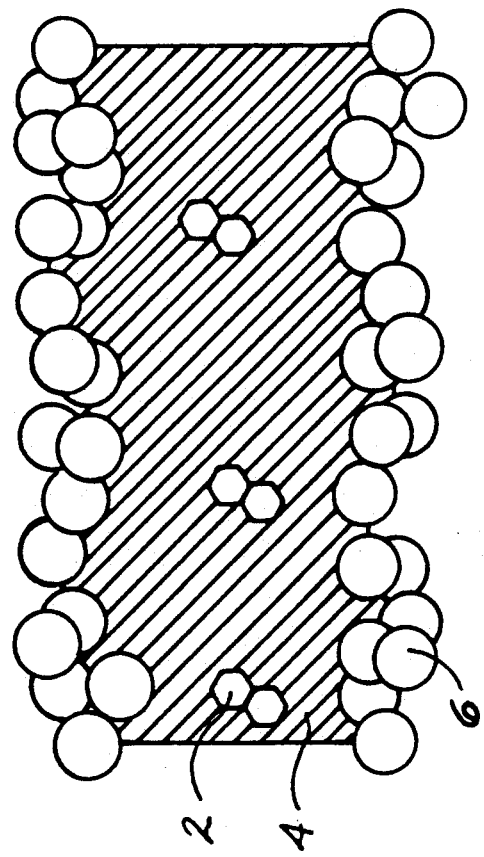
FIG. 1A depicts a fluorophore (2) contained in a solid lipid bilayer made up of hydrophobic moieties (4) and hydrophilic head groups (6).

The purpose of the present invention is to provide a means of detecting lipid layer-soluble chemicals, such as anesthetics, drugs, alcohols, pollutants, and organic chemicals used in industrial processes, which is rapid and accurate in small volumes of gases, liquids, or solids (e.g., tissue). The sensor of the present invention is advantageous because it can be made small, is passive, and is based on optical transduction. Thus, the present sensor has potential use in medical research and clinical practice as a method of determining the presence of or amount of such chemicals in situ in living organisms, including human patients, laboratory animals and the like. Veterinary uses are also contemplated.

In a preferred embodiment, the present invention is directed to a sensor for measuring the presence of and/or the concentration of anesthetics, pollutants in groundwater, industrial organic chemicals in chemical reactors, and lipid-soluble organic chemicals in other relatively inaccessible environments. The analyte must be capable of partitioning into a lipid layer sufficiently to cause a phase change in the lipid layer resulting in a measurable change in a fluorescence characteristic in a fluorophore contained in the lipid layer. The following are examples of types of analytes which could be measured: alkanes, n-alkanols, chloroform, benzene, gasoline, and organic solvents. One preferred class of analyte that can be detected by a sensor in accordance with the present invention is that of anesthetics. General anesthetics are preferred. Specific examples of anesthetics which could be detected are: isoflurane, enflurane, ethanol, and the like.

The present invention allows a determination of the presence of and/or concentration of an analyte in a medium by way of a measurable change in a fluorescence characteristic of a fluorophore contained in a lipid layer to a phase change in the lipid layer that is caused by partitioning of the analyte into the lipid layer. The phase change of the lipid layer is often endothermic; that is, energy is absorbed in passing from a first phase (i.e., a solid phase) to a second phase (i.e., a liquid phase). While not wishing to be limited to a particular theory of operation, the inventors believe that analytes are generally more soluble in one phase of a lipid layer than in another phase. Partitioning or dissolving of an analyte into a lipid layer with an appropriate phase transition is capable of shifting an equilibrium between two phases of the lipid layer at a given temperature.

It is thought that the anesthetic changes the phase transition temperature of the lipid layer for a similar reason that salt lowers the freezing point of water.

In discussing the phase change, it is useful to define an order parameter which describes the state of the lipid layer in terms of its phases. The order parameter is a ratio of the amount of a first phase condition (e.g., a solid phase) to an amount of a second phase condition (e.g., a fluid phase) of a given lipid layer. The order parameter can be conveniently determined for a particular system by taking a ratio of the intensity of fluorescence at two wavelengths that exhibit the largest change as a function of temperature. Experimentally, it is found that the order parameter changes sharply as a function of temperature in a single component lipid layer. Although it may be desirable to use a single component lipid layer for the purposes of the present invention, for many purposes the phase transition will be too sharp for wide usefulness, and an order parameter derived from a single component may not vary in a linear fashion as a function of temperature.

Figure 7:
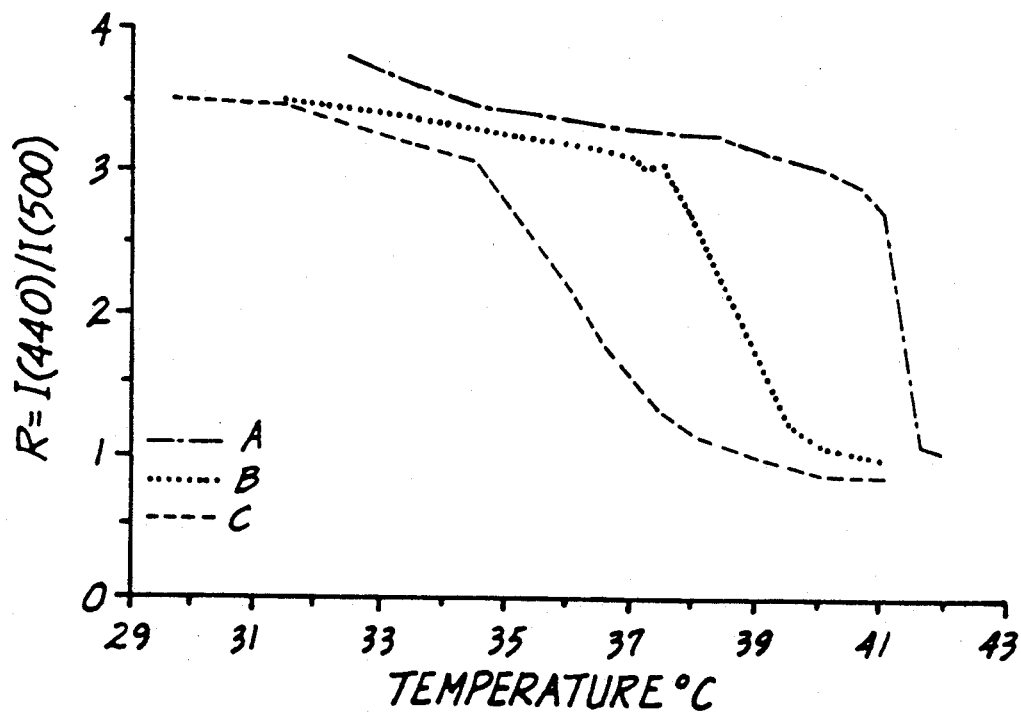
FIG. 7 is a plot of R versus temperature for pure DPPC and DPPC mixed with varying amounts of dimyristoyl phosphatidylcholine (DMPC).

When a mixture of lipid molecules is employed, it is found that the phase transition takes place over a broader range of temperatures. For example, inclusion of cholesterol, which undergoes no phase transition temperature on its own, in a lipid layer having a sharp phase transition temperature will broaden the temperature range over which a phase transition occurs. One of the advantages of a broader phase transition temperature range is that an order parameter derived from the phase transition varies in a more linear fashion with respect to temperature. Combinations of lipid molecules can also be used to adjust the lipid layer phase transition to different temperature ranges with controllable widths. FIG. 7 shows a plot of R, an order parameter expressed as a ratio of fluorescence intensity at two wavelengths, as a function of temperature for a single component lipid layer and multicomponent lipid layers. As more of a second component is added, the phase transition becomes broader with respect to temperature.

Generally, for purposes of the present invention, the lipid layer used must have a phase transition temperature range of finite width, the center of which is within one-half its range of the anticipated operating temperature so that the introduction of the drug, anesthetic, or other analyte will produce as large a change in the lipid layer order parameter as possible. In cases where specific detection is required of a drug that increases the phase transition temperature of a model lipid layer (opposite to the case for most anesthetics), the appropriate lipid mixture for the sensor will have a phase transition just below the anticipated operating temperature. The operating temperature will generally range from about 15° C. to about 42° C. for most biomedical applications, preferably about 20° C. to about 39° C. for biomedical applications. It is also possible for higher or lower temperatures to be involved. In such cases, it will be necessary to choose a lipid layer with appropriate phase transitions relative to the operating temperature. For example, if the analyte is an organic chemical in a high temperature reactor, a lipid layer with a higher phase transition temperature point or range would need to be used.

In general, as the lipid layer, there may be used any amphiphilic molecules which associate with each other into monolayers or bilayers which have a reversible phase transition involving a change in order of the lipid molecules making up the lipid layer. In a preferred embodiment, phospholipids with saturated $C_8$-$C_{20}$ hydrocarbon chains are used. Preferred examples are dipalmitoyl phosphatidylcholine, dimyristoyl phosphatidylcholine, and mixtures thereof. The lipid layer may range in thickness from about 50 angstroms to about 500 microns, preferably about 0.1 to about 100 microns.

The lipid layer, which contains the fluorophore, could be suspended in solution, such as in a cuvette, when it is contacted with the medium suspected of containing the analyte. For many applications, it will be convenient to place the lipid layer containing the fluorophore on a substrate to facilitate contacting of the sensor with the medium suspected of containing the analyte. The lipid layer may be noncovalently attached to the substrate, or covalently attached to the substrate. It may also be desirable to immobilize a lipid layer on a substrate to prevent lipid molecules and/or fluorophore molecules from escaping into the medium. Embedding the lipid layer in a hydrogel has been shown to produce desirable results. As the hydrogel, there may be used agarose, polyacrylamide, gelatin, and the like.

In other applications, it may be desirable to separate the medium suspected of containing the analyte and the lipid layer by providing a membrane between the lipid layer and the medium. Selectively permeable membranes placed around a lipid-fluorophore sensor could be used to create selectivity. For example, porous polytetrafluoroethylene, (e.g., Teflon®) could be employed as the membrane to allow selective analysis of gaseous analytes. It is also contemplated, in accordance with the present invention, to separate the sensor from the medium by a hydrophilic membrane containing immobilized therein an enzyme, such as one which is capable of degrading interfering analytes.

No particular limitation is placed on the manner in which the lipid layer is placed on a substrate, as long as it can be contacted with the medium. Some illustrative arrangements of lipids are shown in FIGS. 3A-3E. These are described in greater detail hereinbelow.

Figure 3A:
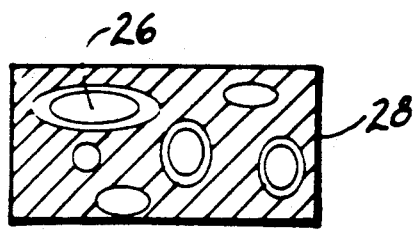
FIGS. 3A-E show several possible arrangements of lipid layers containing fluorophores which could be brought into contact with a medium containing an analyte for determining the amount or presence of the analyte in accordance with a method of the present invention.

In FIG. 3A, an embodiment is shown in which fluorophore-containing liposomes (26) are immobilized, either in a containment vessel such as a porous fiber, and/or in a hydrogel such as polyacrylamide, agarose or gelatin (28). The hydrogel can then be either coated on the core of the fiber for interaction with the evanescent field or placed as a bulk sample at the end of one or more fibers.

Figure 3B:
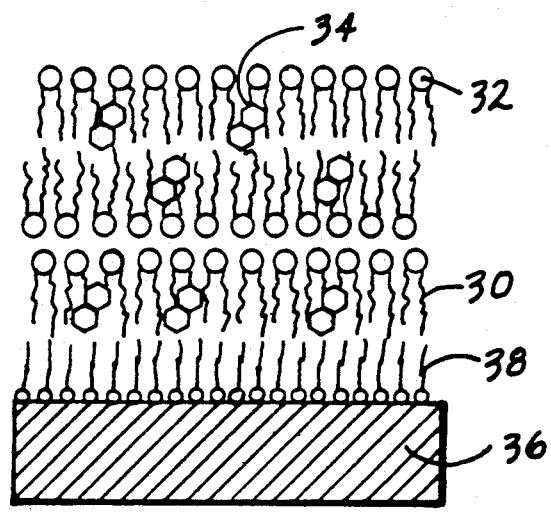

FIG. 3B shows an embodiment in which an optical surface (36), for example an optical fiber, is coated with a substance (38) that renders the fiber hydrophobic, such as an organosilane (e.g., dimethyloctadecylchlorosilane), and the fiber is coated with one or more layers of lipid (30 and 32) containing fluorophore molecules (34). The lipid layers are adhered to the fiber by conventional techniques, such as Langmuir/Blodgett techniques, precipitation from organic solvent to which water is added, detergent dialysis, or simple insertion of the fiber into an aqueous suspension of liposomes. Interaction with the fluorescence exciting radiation is either by direct contact therewith, or by placement at the terminus of a single fiber.

Figure 3C:
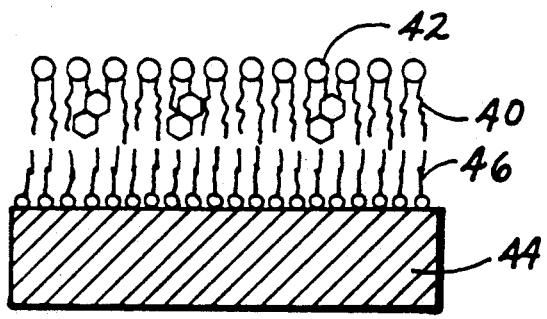

FIG. 3C shows an embodiment in which an optical surface (46), for example, that of a fiber, is first coated with a substance that renders the fiber surface hydrophobic (48). This substance may be generally any molecule with one end capable of being linked to the surface and another end which is a hydrophobic chemical moiety. Organosilanes are one preferred example; specifically, dimethyloctadecylchlorosilane could be used. After rendering the surface hydrophobic by reaction with the substance, such as an organosilane, a single monolayer of a lipid (40) containing a fluorophore (42) is deposited on the hydrophobic surface by any of the above-mentioned techniques.

Figure 3D:
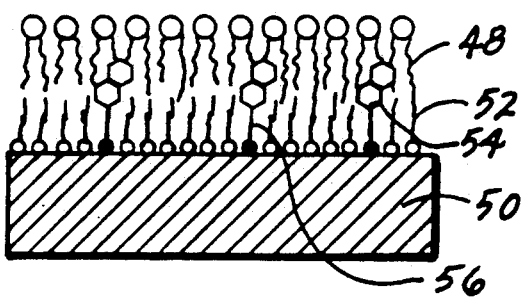

FIG. 3D shows an embodiment in which an optical surface (50), such as that of a fiber, is coated with a substance that renders the fiber hydrophobic (56), in the same manner as discussed in FIG. 3C, and also some part of the optical surface is covalently attached via linkers (52) to fluorophore molecules (54). The surface is then covered by a monolayer of lipid (48) having an appropriate phase transition temperature.

Figure 3E:
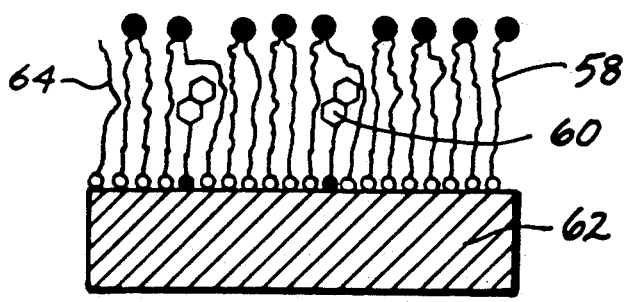

FIG. 3E shows an embodiment in which a part of an optical surface (62), such as that of a fiber, is covalently attached to fluorophores (60), and the remaining part of the optical surface is attached to amphiphilic molecules (58) having one or more hydrocarbon chains that are covalently linked via linkers (64) to the surface.

The fluorophores which are useful in the present sensors must be capable of partitioning into the lipid layer. By "partitioning" is meant that the fluorophore dissolves in at least one phase of the lipid layer. The fluorophores of the present invention must also have a fluorescence characteristic that changes when the phase of a surrounding lipid layer changes. This fluorescence characteristic can be any one which is measurable by standard techniques. For example, the variable fluorescence characteristic could be fluorescence intensity at a given wavelength, a shift of the wavelength of maximum fluorescence intensity, the lifetime of a fluorescent excited state of the fluorophore, and the like. Preferably, the fluorophore will be of the type that changes its fluorescence emission spectrum or excited state lifetime when the lipid layer undergoes a phase change.

The following structure shows the most general design for a useful fluorophore, consisting of a fluorophoric core F that responds to changes in the phase of the lipid layer, a hydrophobic anchor region H, and a polar region P that keeps part of the fluorophore near the polar region of the lipid layer in which the molecule is embedded.

H-F-P

In this general structure, H may include: n-alkanes, branched alkanes, alkenes, and alkynes, and derivatives of these groups with functionalized terminal moieties that allow covalent attachment of the molecule to a substrate. The F group can include: naphthalene, anthracene, pyrene, and other aromatic fluorophore groups. P can include ammonium, alkyl ammonium, and other polar groups, such as carbohydrates or polyoxyethylenes.

Particularly preferred fluorophores are those which change emission spectra and/or excited state lifetime. These fluorophores are of particular utility in sensors because they provide a signal, the quantitative interpretation of which is not affected by such interfering optical phenomena as bending of fibers, system degradation, source intensity fluctuation, dye photobleaching, or coating of optics with dirt. If baseline intensities are known, a determination of the ratio of phases in a given lipid layer can be made by obtaining a simple ratio of fluorescence emission at two wavelengths $[R=I(\lambda_1)/I(\lambda_2)]$. The sensitivity of these fluorophores to lipid layer phase transitions is believed to be partially due to the residence of the fluorophore near the polar region of the lipid layer. It may be advantageous to alter this residence position by changes in the structure of the fluorophore in order to alter the sensitivity of a fluorescence characteristic of the fluorophore to phase transitions. Changes in the structure of the fluorescent probe, resulting in a variation in the equilibrium depth of the probe molecule in the lipid layer environment, will allow selectivity between different classes of drugs known to partition into different regions of lipid layers. Such structural changes can be carried out by one of ordinary skill in the art based on conventional techniques.

Specific examples of desirable fluorophores are: Patman, Laurdan and Prodan. The structures of these fluorophores are as follows:

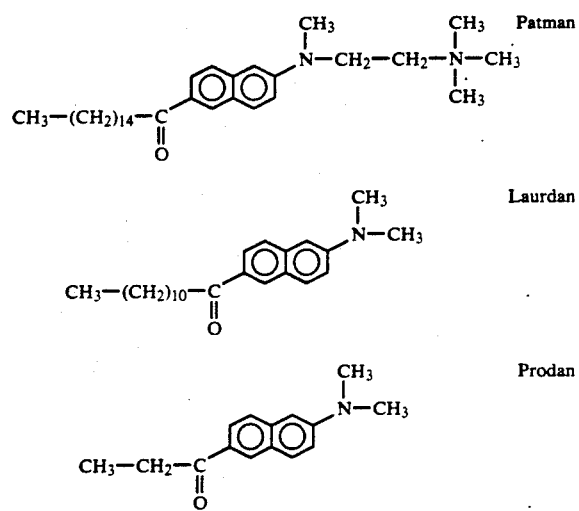

Derivatives of known fluorophores, such as Patman, Laurdan, and Prodan, may also be used for purposes of the present invention. For example, a naphthalene group may be moved up or down relative to a charged amine functionality. Also, changes may be made in the hydrocarbon chain length or type, thereby affecting structure and solubility of the fluorophore. In order to facilitate the maintenance of the fluorescent probe deep in the hydrophobic region, and to reduce its solubility in aqueous solvents, it may be desirable to remove the charged quaternary ammonium group of Patman, replacing it with other groups, such as uncharged groups. It is possible that the naphthalene core of the fluorophore may not be optimal for all embodiments of the sensor if, for example, it proves advantageous to shift absorption or emission spectra to different spectral regions. Replacement of the terminal methyl group with a reactive functional group, such as a methoxysilyl group, would allow the entire molecule to be covalently attached to a substrate.

Some generic structures based on the above concepts, which are contemplated as fluorophores for use in the present invention, are given below. While some of the following structures are based on Patman, similar alterations are contemplated for Laurdan and Prodan, as well as other known fluorophores.

The following structure covers alterations in the Patman structure to move the naphthalene group up and down relative to the charged head group by varying Y, and changes in the hydrocarbon chain length or type by varying X, thereby affecting structure and solubility.

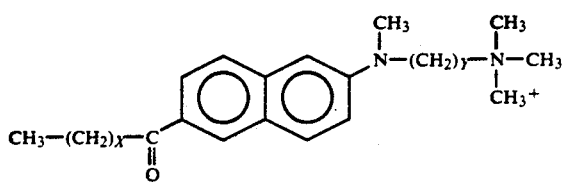

wherein $X=0-25$ (preferably 8-12) and Y is 2-16 (preferably 2-10).

The following generic structure includes replacement of the terminal methyl group to allow the entire molecule to be covalently attached to a substrate by addition of a reactive functional group Z such as a silyl group. Again, X can range from 0-25 and Y can range from 2-16.

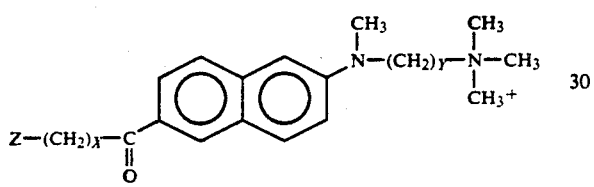

In order to facilitate the maintenance of the fluorescent probe deep in the hydrophobic region and to reduce its solubility in aqueous solvents, the following structure includes a W group in place of the ammonium group in Patman.

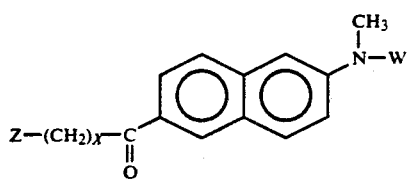

W can include the following: H, $CH_3$, or polar groups such as carbohydrates or polyoxyethylenes.

In the following generic structure, the naphthalene group itself is variable, in terms of F in the structure:

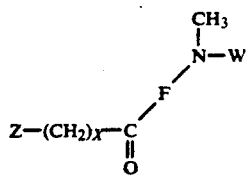

The F group can include the following: naphthalene, anthracene, pyrene, and other aromatic fluorophores. The other variables remain the same.

One reason that fluorophores based on the 6-keto-2-dialkylaminonaphthalene structure, such as Prodan, are preferred for the purposes of the present invention is that their excited states have a much higher dipole moment than their ground state. This property is responsible for the high solvent sensitivity of the fluorescence emission of this family of fluorophores, and why the change in lipid bilayer phase state can be transduced as a shift in fluorescence emission. Other fluorophores, such as p-aminobenzylidene malononitriles, which have very polar-excited states, may also be very well suited for the present purposes. In view of these considerations, the fluorophores that are useful for purposes of the present invention are generally those with highly polar excited states as compared to their ground states.

Synthesis of any novel fluorophore derivatives may be carried out by standard organic chemistry reactions reported in the literature.

The most preferred fluorophore for the purposes of the present invention is Laurdan.

Temperature determination for calibration of the fluorescence characteristic response can be either by a reference sensor, or by another type of temperature sensor that can be placed near the lipid sample.

PROBE DESIGN

As described above, the present sensors, which comprise a lipid layer with suitable phase transitions and a fluorophore, may be adhered to or attached to an optical substrate which serves as an optical waveguide. In this manner, fluorescence exciting radiation can be transmitted to the sensor, and emitted fluorescence radiation can be carried away from the sensor to a detector. In a general embodiment, a single optical waveguide can be utilized both for transmission of the exciting radiation to the sensor and transmission of emitted fluorescence by the sensor to a detector. Alternatively, more than one optical waveguide can be utilized, at least one for transmitting fluorescence exciting radiation to the sensor and at least one other optical waveguide for transmitting emitted fluorescence away from the sensor.

In a preferred embodiment, the optical waveguide is an optical fiber. When an optical fiber is used as the optical waveguide, the sensor and optical waveguide assembly is collectively referred to in a general sense as a probe, and in the particular case wherein optical fibers are used as the optical waveguide, the probe is referred to as an optrode.

Figure 5:
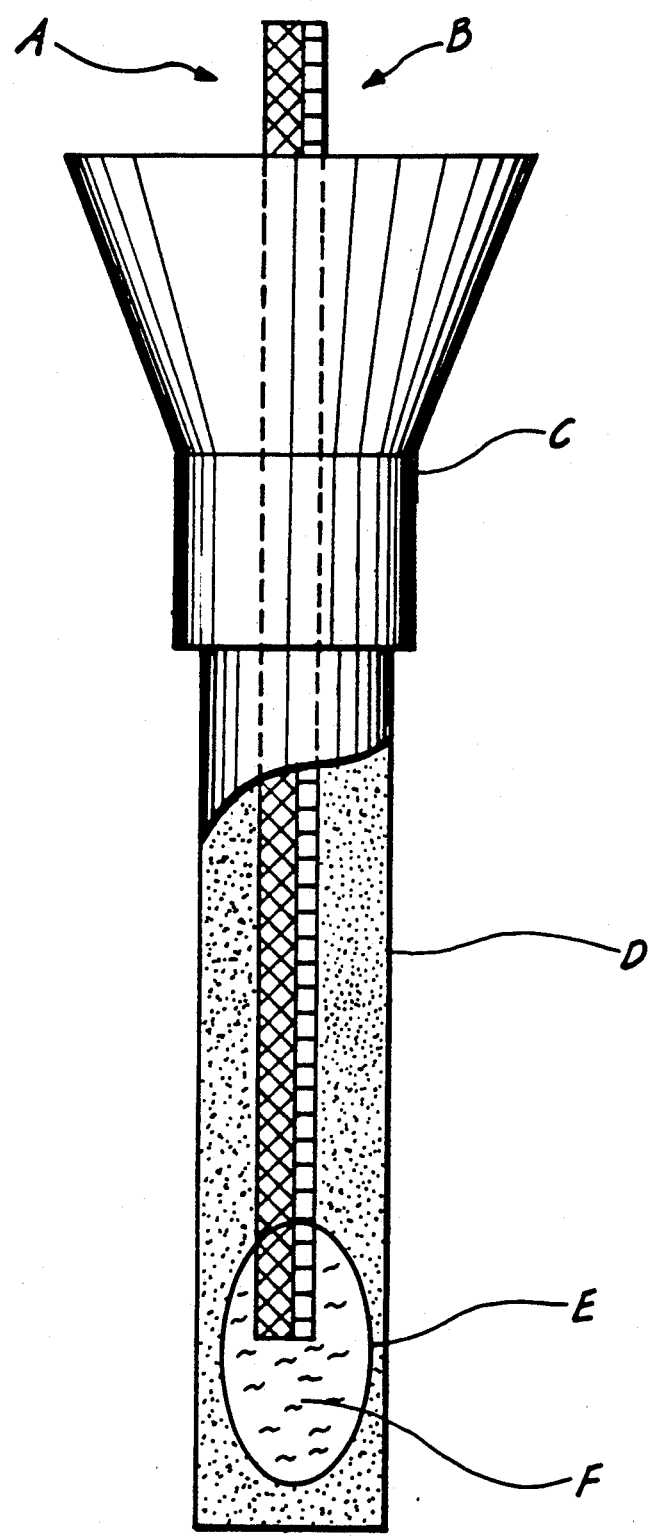
FIG. 5 is a depiction of an optrode of the present invention.

A specific embodiment of an optrode of the present invention is depicted in FIG. 5. In this example, the medium is allowed to come into contact with a lipid layer containing a fluorophore by way of a side hole in a needle. The sensor of the present invention, which in the example shown in FIG. 5 is made up of liposomes containing therein fluorophore molecules, may conveniently be attached to the end of one or more optical fibers for transmitting and collecting fluorescence radiation. Also, in the particular example shown in FIG. 5, liposomes making up the sensor have been immobilized in a hydrogel, such as agarose, polyacrylamide, or gelatin. Immobilization is an optional element of the present invention for maintaining the lipid layer in close proximity to a substrate.

SYSTEM OF THE PRESENT INVENTION

When a sensor of the present invention is viewed in combination with other elements, such as a device for emitting fluorescence radiation and devices for collecting and measuring emitted fluorescence radiation, and the like, the resulting assembly is referred to as a system herein. Systems of the present invention can include sensors which are either directly attached to other devices by way of optical waveguides, or can include systems wherein there is no optical waveguide, such as a cuvette containing a sensor of the present invention in combination with a fluorescence excitatory source and detector.

In a preferred embodiment, one or more optical waveguides are attached to the sensor of the present invention, and the optical waveguides are in turn attached to a source for exciting radiation and/or a device for measuring emitting fluorescence radiation.

Figure 4:
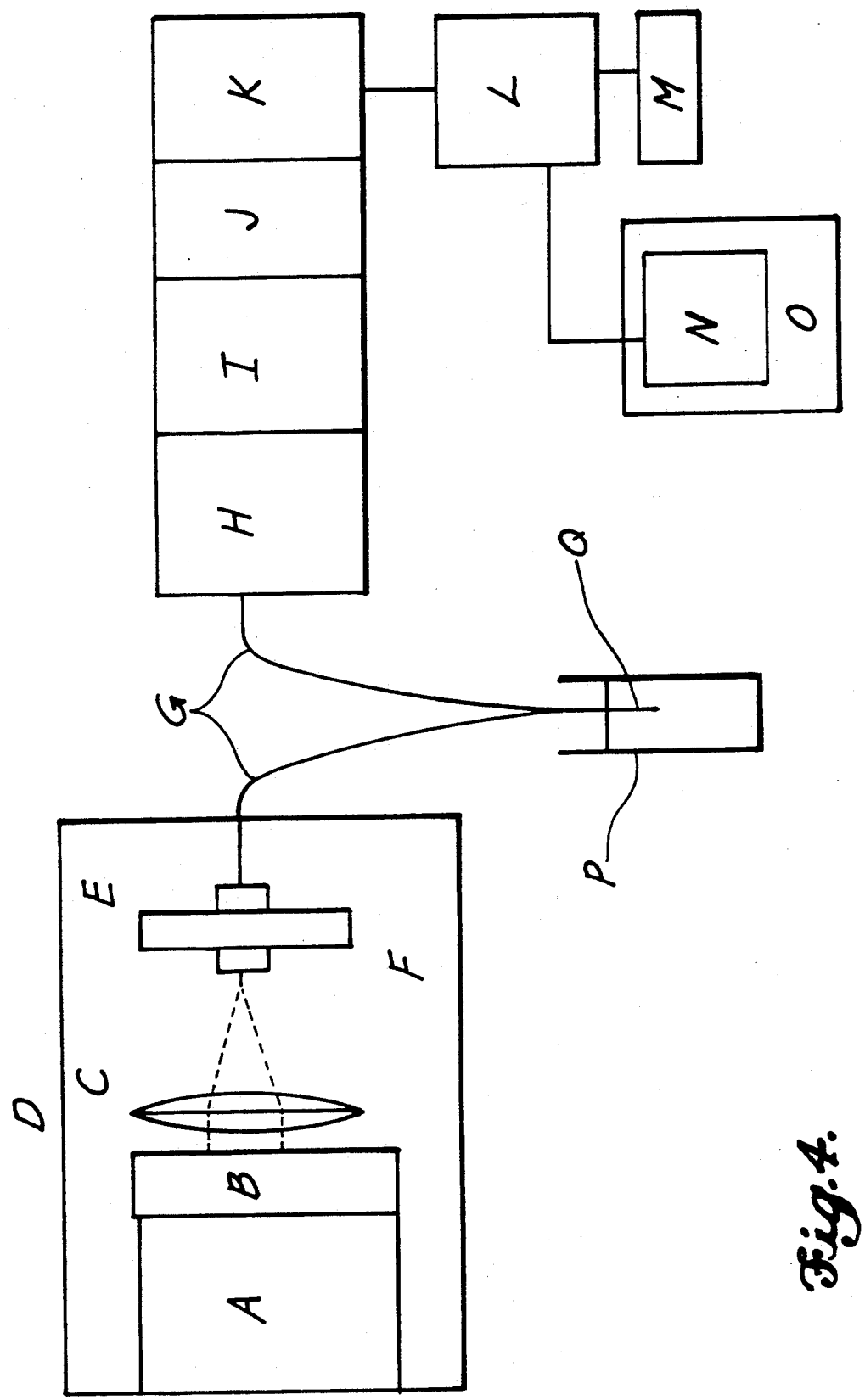
FIG. 4 shows a system including an optrode of the present invention.

In a further preferred embodiment, the waveguides of the system are optical fibers. FIG. 4 shows an optrode of the present invention in combination with other devices for providing fluorescence excitatory radiation and collecting and measuring emitted fluorescence radiation. Thus, FIG. 4 shows an embodiment of a system in accordance with the present invention.

In general, as the source of exciting radiation, any conventional source may be used. Representative examples include incandescent sources, arc lamps, light-emitting diodes, and lasers. If the source does not already produce monochromatic light, it will be necessary to include one or more filters or monochromators to render the light monochromatic. Fluorescence emitted by the fluorophore in the sensor will generally be rendered monochromatic in a similar manner by use of a monochromator with or without various filters to eliminate scattered light, or a beam splitter combined with one or more filters to produce two beams at different wavelengths. Representative detectors of fluorescence include photomultipliers, semi-conductor devices such as photodiodes, and a position sensitive detector. In addition to the above devices, the system may also include analog and digital circuitry in order to collect and analyze data. In all cases where specific devices have been mentioned herein, equivalents thereof are also contemplated. Specific examples of these various elements are depicted in FIG. 4.

In a preferred embodiment, the detection device should be capable of comparing fluorescence signals from a sensor in contact with a sample and a reference sensor. If changes in the sample fluorescence emission spectrum are to be used for measurement of the presence of or amount of the analyte in a medium, the fluorescence detection device should be capable of comparing the fluorescence intensity in at least two wavelengths, either simultaneously or sequentially. Alternatively, if the fluorescence lifetime of a fluorophore is used, a single emission wavelength will suffice.

Additional details of preferred sensor, probe and system design are provided in the following examples. However, the present invention is not to be interpreted as limited to the following exemplified preferred embodiments, and may be practiced in all ways equivalent to the preferred embodiment, as understood by one of ordinary skill in the art. Additionally, some features are described which are optional (e.g., the immobilizing hydrogel).

EXAMPLE OF SENSOR DESIGN

Materials and Methods

Lipids and other reagents. Dipalmitoyl-L-α-lecithin (DPPC, M.W. 734.05) and dimyristoyl-L-α-lecithin (DMPC, M.W. 677.95) in chloroform solution at a concentration of 20 mg/ml were purchased from Avanti Polar Lipids Inc. (purity >99%) and were used without further purification. Laurdan (M.W. 353) was obtained from Molecular Probes and was dissolved in chloroform at the concentration of 1 mg/ml. Agarose (molecular biology reagent No. A-9539) was purchased from Sigma. Its gel point, that is, the temperature measured during cooling at which an aqueous agarose solution forms a gel, is 36° C. Once formed, a gel remains "stable" up to its melting point of about 90° C.

Lipid Layer Preparation. Fluorophore-containing hydrated lipid was prepared as follows. Fluorophore and lipid solutions were mixed at the molar ratio of one probe molecule per 150 lipid molecules (1:150). When lipid mixtures had to be prepared, the different lipids were mixed in chloroform solution. The solvent was evaporated in an Evapotec Micro Rotary Film Evaporator (Haake Buchler instruments, Inc.) while the container was warmed in the water bath to 40° C. In order to eliminate any trace of solvent, the sample was then stored under vacuum for 8 hours. Dried lipid was then hydrated with buffer (10 mM HEPES/100 mM NaCl in distilled deionized water, pH 7.5) to yield different lipid concentrations. Usually, the samples were stored in the refrigerator overnight and the vesicles prepared on the next day by the following method. Hydrated lipid samples, kept always at a temperature above the phase transition, were dispersed by vortex mixing for a total of 10 min.

PHASE TRANSITIONS IN PHOSPHATIDYLCHOLINE LIPOSOMES

Dipalmitoyl phosphatidylcholine (DPPC) and dimyristoyl phosphatidylcholine (DMPC) were investigated because their phase transition temperatures in pure form are close to a desirable sensor operating range for biomedical applications: around 41.4° C. for DPPC and 23.7° C. for DMPC. Also, they have similar structures, which facilitates bilayer formation. The lipid molecules were mixed in chloroform solution. The experimentally-determined effect of temperature changes on fluorescence characteristics of Laurdan-containing DPPC and DMPC liposomes is shown in FIG. 7. Data was collected on aqueous suspensions of liposomes in cuvettes with a PE LS-5B luminescence spectrometer.

General method of entrapment of liposomes in agarose gel. Agarose gel in the range of 1 to 2% (1 g-2 g of a agarose in 100 ml of buffer) was prepared by hydrating agarose powder with buffer. The aqueous agarose solution was then held above the gelling temperature for 10 min. The solution of liposomes in buffer, which had been kept above the phase transition temperature after vortexing, was then mixed into the gel at the desired concentration. The sample was then allowed to cool to room temperature for gelation.

DEMONSTRATION OF THE USE OF HYDROGELS FOR IMMOBILIZATION OF PHASE-SENSITIVE LIPOSOMES

Fluorescence measurements were carried out in far UV-VIS spectrophotometric cuvettes (Spectrocell Corporation). The temperature was monitored inside the cuvette with a teflon-coated thermocouple connected to a Sensortek BAT-10 digital thermometer with a resolution of 0.1° C. Fluorescence emission spectral measurements were performed on a Perkin-Elmer, LS-5B luminescence spectrometer with a 4 position thermostatically controllable cell holder. A thermostatically controlled water bath and pump Neslab RTE- 110, with a programming controller was connected to the cell holder. Data were acquired using a RS-232C Interface for a Zenith (IBM compatible) computer. For recording of emission spectra of Laurdan, the excitation wavelength was 350 nm. The spectral resolution as determined by slit widths were 5 and 3 nm for excitation and emission, respectively. A scanning speed of 120 nm/min was chosen.

Figure 6:
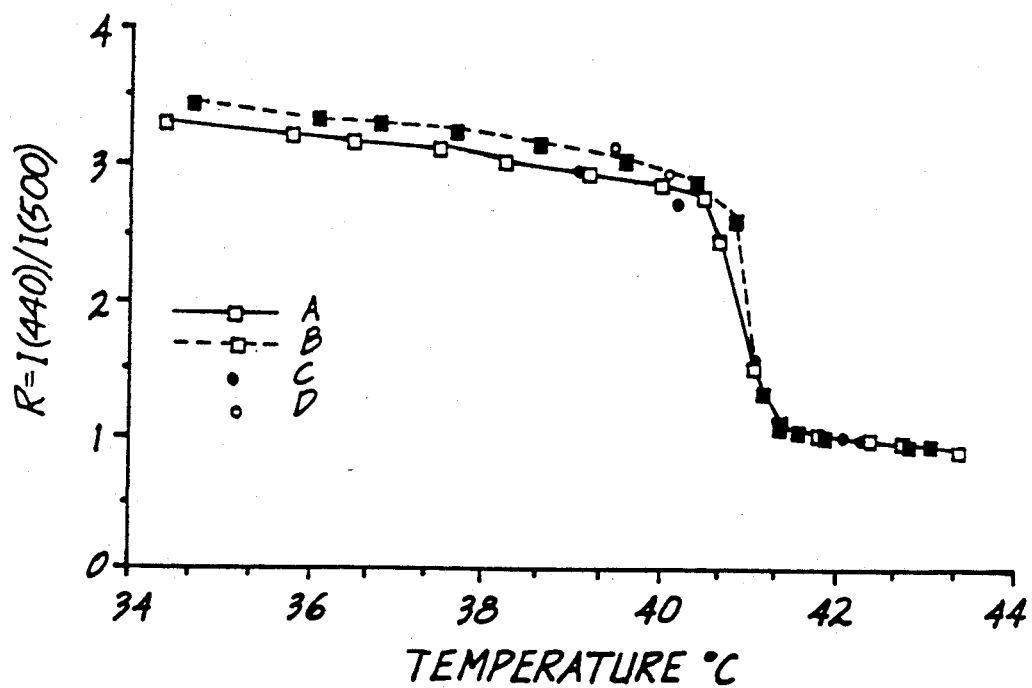
FIG. 6 is a plot of the ratio (R) of intensity of fluorescence emission of Laurdan at the two wavelengths 400 nm and 500 nm [R=I(440)/I(500)] versus temperature for pure dipalmitoylphosphatidylcholine (DPPC) liposomes in aqueous suspension and entrapped in agarose gel (a hydrogel for immobilizing the DPPC liposomes).

The effect of agarose gel on the phase transition of Laurdan-containing DPPC liposomes was studied by comparing two samples prepared as follows. A buffered suspension of DPPC at a concentration of 0.28 mg/ml was vortexed for 10 min at a temperature above 45° C. In one cuvette, 1.5 ml of this solution was diluted with 1.5 ml of buffer leading to a final concentration of 0.14 mg/ml. In another cuvette, 1.5 ml of lipid solution was mixed with 1.5 ml of 2% agarose gel. Fluorescence spectra collected at different temperatures from Laurdan-containing DPPC liposomes entrapped in agarose gel and in aqueous solution demonstrated that the phase transition can best be monitored by taking the ratio of emission intensities at 440 nm and 500 nm. The plots of the ratio $R = I(440)/I(500)$ versus temperature for DPPC liposomes in aqueous solution and for DPPC liposomes entrapped in agarose gel are reported in FIG. 6. Data are reported for a first heating scan followed by a cooling scan. The presence of the gel does not substantially affect the phase transition of DPPC liposomes. Thus, agarose gel can be used for immobilizing phospholipid liposomes at the end of an optical fiber in a sensor.

DEMONSTRATION OF THE SENSITIVITY OF LIPOSOMES CONTAINING LAURDAN TO VARYING CONCENTRATIONS OF GENERAL ANESTHETICS

Figure 8:
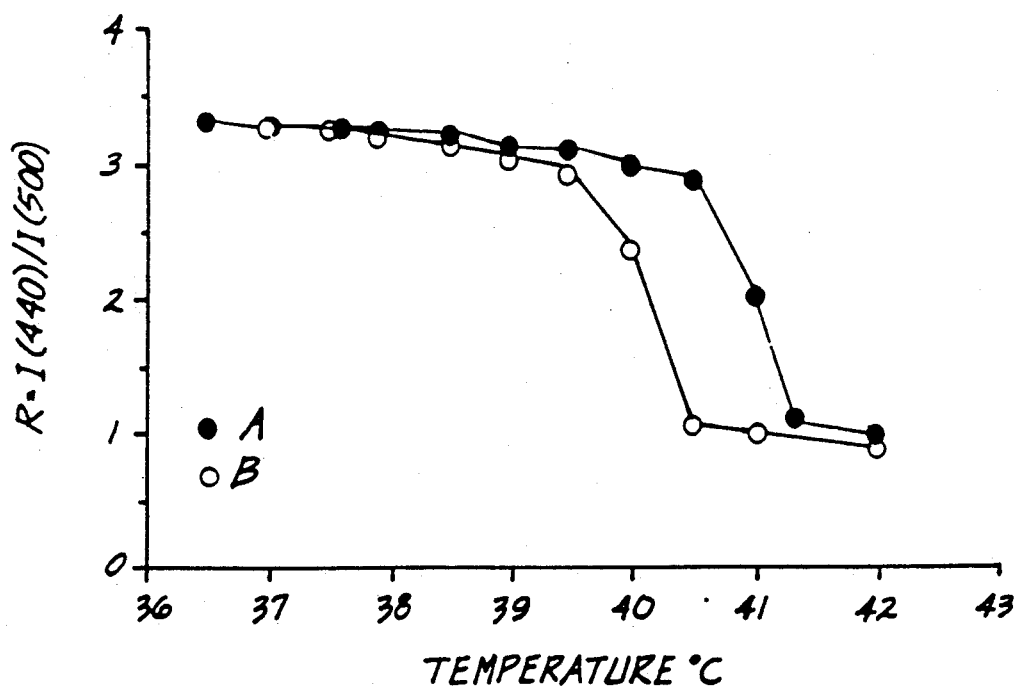
FIG. 8 depicts the sensitivity of liposomes containing the fluorophore Laurdan, to the presence of varying concentrations of the anesthetic isoflurane. For isoflurane, 1MAC, the concentration of anesthetic in the lungs that results in anesthetization in 50% of patients, is 1.15% of 1 atmosphere (the partial pressure of isoflurane in inhaled gas).
Figure 9:
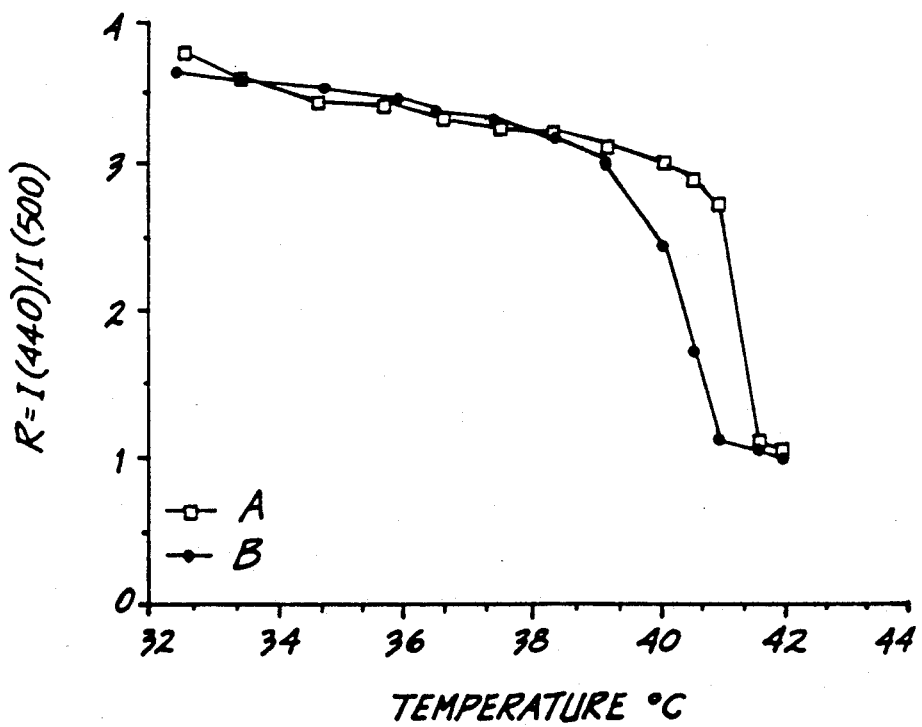
FIG. 9 shows the sensitivity of Laurdan-containing liposomes in aqueous solution to the presence of 5 mg/ml ethanol.
Figure 10:
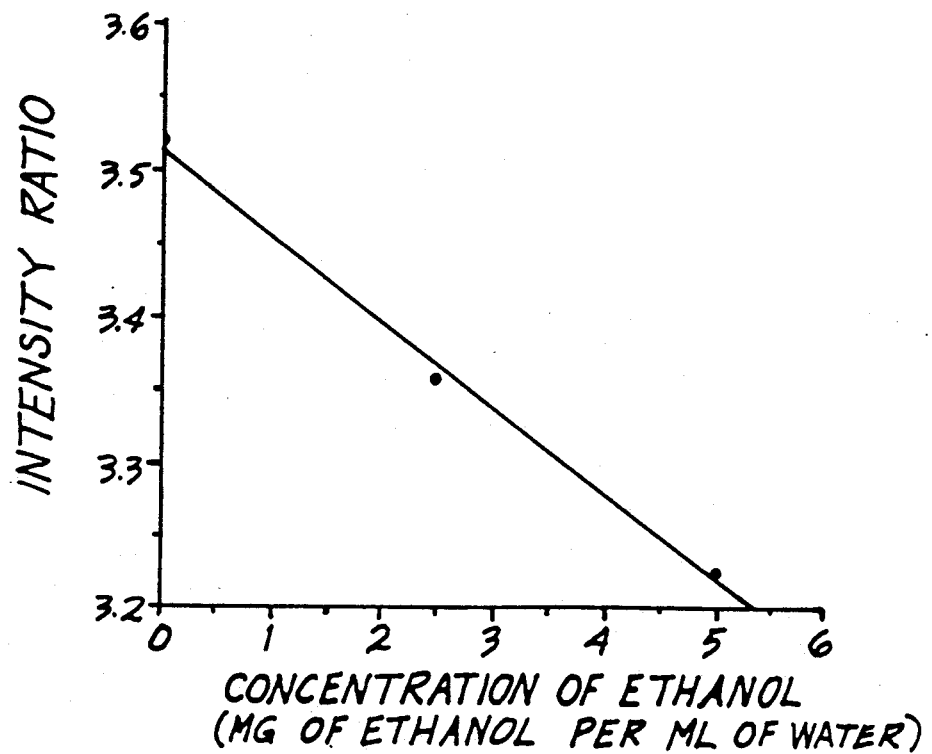
FIG. 10 shows the fluorescence response of a probe to varying concentrations of ethanol.
Figure 11:
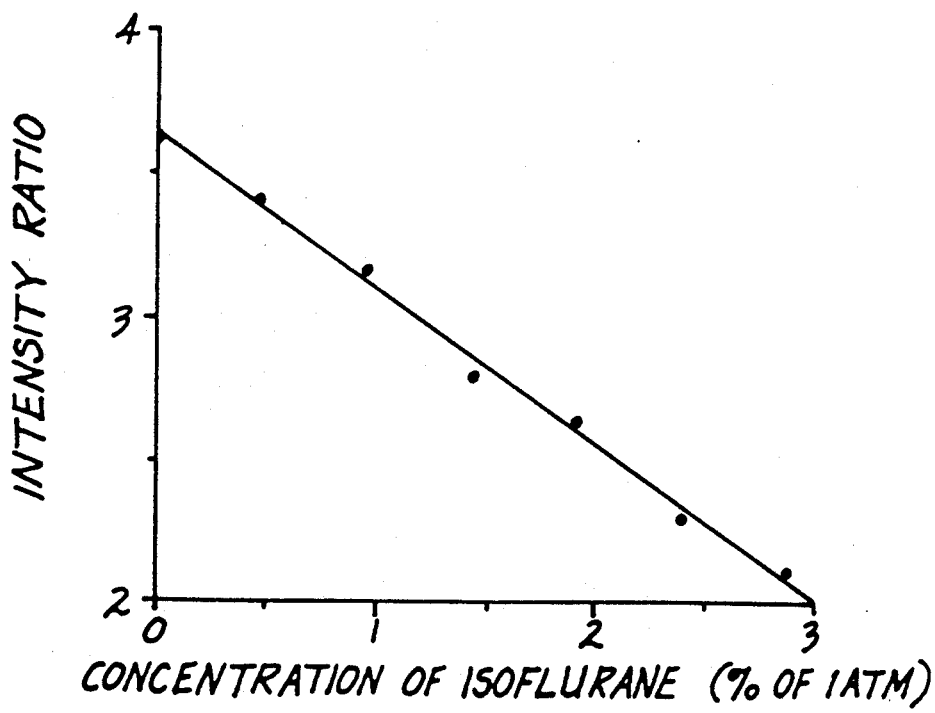
FIG. 11 shows the fluorescence response of a probe to varying concentrations of the general anesthetic isoflurane.
Figure 12:
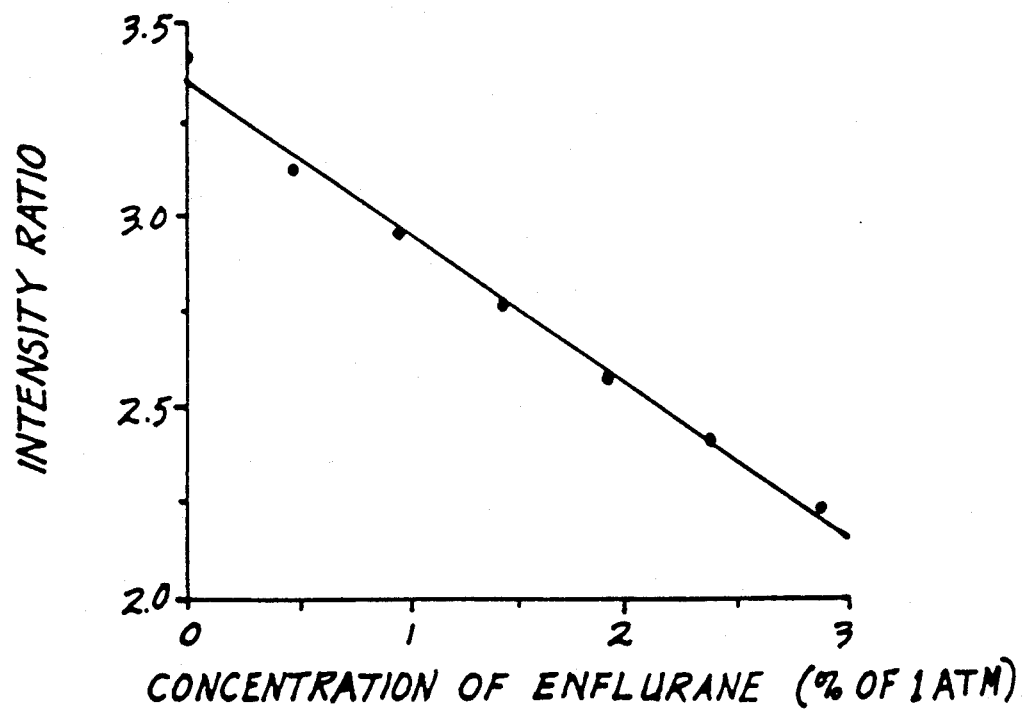
FIG. 12 shows the fluorescence response of a probe to varying concentrations of the general anesthetic enflurane.

It was demonstrated that DPPC liposomes containing Laurdan are sensitive to the presence of the commonly used general anesthetic isoflurane in clinically relevant concentrations. The plots of the ratio $R = I(440)/I(500)$ versus temperature for DPPC liposomes in aqueous solution in the presence of anesthetic (concentration of isoflurane of 1.4%) and without anesthetic are reported in FIG. 8. The plots of the ratio $R = I(440)/I(500)$ versus temperature for DPPC liposomes in aqueous solution in the presence of ethanol (5 mg/ml) and without ethanol are reported in FIG. 9.

FIBER-OPTIC APPARATUS AND OPTRODE DESIGN

Source. An optical microscope was used as input stage. The source consisted of a short arc mercury lamp followed by a bandpass filter with a transmissivity centered at 365 nm and a bandwidth of 11 nm. The excitation light was focused by a microscope objective lens (N.A. = 0.45) onto one end of the input optical fiber, placed in a fiber-holder of a x-y positioner used for the alignment. The 365 nm radiation excites fluorescence in the fluorophore-containing liposomes trapped at the other end of the fiber.

Spectrometer. Radiation consisting of the scattered light at 365 nm and the emitted fluorescence was collected by a second optical fiber. The output end of this fiber was coupled into the spectrometer Chemspec 100S (American Holographic, Inc.). This very compact spectrometer features a low f number (f/2.2) for fiber-optic input, a direct fiber-optic input connector, a detector mounting block for diode array, and interchangeable gratings. Preferably, an aberration corrected holographic diffraction grating with a resolution of 1.8 nm in the range 300-800 nm is used.

Detector. The detector was an EG&G Reticon "S" series Self-Scanning Linear Photodiode Array (RL0512S). It consists of 512 diodes. To reduce stray light due to the 365 nm component and the intrinsic limitations of the diffraction grating which would reach the diode array and be detected as background noise, a high pass filter was placed in front of the detector.

Data acquisition. The system for acquisition and storage of data was a multifunction high speed analog/digital I/O expansion board (DASH-16 from MetraByte Corporation) internally installed in an IBM/XT Personal Computer. By using the D.M.A. capabilities of the IBM P.C., DASH-16 is able to provide high data throughput (conversion/sec).

Software. The utility software for DASH-16 used in the data acquisition custom software consisted of a machine language driver (DASH16.BIN) for control of A/D, digital I/O channel functions, and data transfer via BASIC CALL and also consisted of initial setup and installation aids.

A preferred optrode design was based on a 18 gauge disposable needle with a side hole. A 200 μm diameter high N.A. (N.A. = 0.45) fiber was used for the excitation and a 110 μm diameter high N.A. fiber (N.A. = 0.45) was used for fluorescence collection. The two optical fibers were first glued together and then inserted into the needle and immobilized so that the extremities were at the level of the side hole. Then, a drop of warm agarose-liposome suspension was deposited through the side hole and gelation occurred around the fibers. A schematic drawing of the optrode is reported in FIG. 5.

DEMONSTRATION OF OPTRODE SENSITIVITY

The sensitivity of the optrode to changes in temperature has been demonstrated by collecting fluorescence spectra at different temperatures using the fiber-optic apparatus. The same device consistently showed ample sensitivity to clinically relevant concentrations of anesthetics in the gas phase, and demonstrated sensitivity to ethanol.

A BIOMEDICAL SYSTEM

A system based on the above-described sensor could be constituted as follows. A probe consists of some optical element coupled to a lipid layer (e.g., a lipid bilayer or immobilized liposomes). The lipid layer is so constituted as to have an order-disorder hydrocarbon chain phase transition of finite width near or just above or below (preferably above) the temperature range at which the probe is designed to operate. Incorporated into the lipid member is a fluorophore that is sensitive to changes in the phase of the lipid layer. In addition there should be a method of determining the exact temperature of the sensor. The preferred method for determining the temperature is to use an identical lipid-based reference sensor that is coated by a material (e.g., a membrane) that is impermeable to anesthetics and similar substances in the experimental time scale. The two probes must be held in close proximity to insure identical temperatures in both lipid layers. The fluorescence is excited and analyzed by a set of optics and electronics that may be in contact with the two sensors, or may be separated from them by a length of optical fiber.

ADVANTAGES

The sensors of the present invention exhibit a number of advantages as compared to existing sensors and provide a technique that is advantageous over existing techniques for detection of analytes, such as anesthetics in particular. Some of these advantages are:

1. The sensor described herein will respond to a variety of analytes such as hydrocarbons, alcohols, and other chemicals that partition into the lipid bilayer. For fluorophores such as Laurdan, the technique is not based on quenching of fluorescence.

2. The sensor itself can be as small as the tip of an optical fiber, and the lipid layer can be as thin as about 50 angstroms, allowing both a rapid response (a few seconds is sufficient) and potential placement of the probe within small veins and arteries, or directly within tissue.

3. The use of a fluorophore, such as Laurdan, that transduces a lipid layer phase change into a wavelength shift is uniquely useful for a sensor. This alleviates the problems associated with transduction into a change in intensity. Changes in the degree of fiber bending, photobleaching, quenching by oxygen, coating of the optics with dust and dirt, and long-term degradation of the optical elements, including detectors, can all alter the intensity of a measured fluorescent signal. When the fluorophore's emission wavelength shifts as is the case with Laurdan, measurement at two wavelengths allows a unique determination of the state of the molecule, and hence the concentration of an analyte.

After reviewing the foregoing specification, one of ordinary skill in the art will be able to make various changes, substitutions of equivalents, and other alterations without departing from the broad concepts disclosed herein. It is therefore intended that protection afforded by Letters Patent of the United States hereon be limited only by the definition contained in the appended claims and equivalents thereof.

The embodiments of the invention in which an exclusive property or privilege is claimed are defined as follows:

1. A sensor for use in the determination of the presence or amount of a lipid-soluble analyte in a medium, comprising:
   a lipid layer capable of dissolving the analyte, the lipid layer having a first phase condition in the absence of the analyte and a second phase condition, different from the first phase condition, in the presence of the analyte, said dissolving causing a phase change of the lipid layer from the first phase condition to the second phase condition in a manner related to the amount of the analyte dissolved therein, and a fluorophore contained in the lipid layer, the fluorophore having a fluorescence characteristic that varies in response to the phase change of the lipid layer from the first phase condition to the second phase condition, wherein said lipid layer is in the form of liposomes immobilized on a porous fiber or in a hydrogel.

2. A sensor in accordance with claim 1, wherein the fluorophore is such that the fluorescence characteristic is the wavelength of maximum intensity of fluorescence emission by the fluorophore, the lifetime of a fluorescent excited state of the fluorophore, or a combination thereof.

3. A sensor in accordance with claim 1, wherein said liposomes are immobilized in a hydrogel which comprises polyacrylamide, agarose, or gelatin.

4. A sensor in accordance with claim 1, wherein the liposomes comprise dipalmitoyl phosphatidylcholine, dimyristoyl phosphatidylcholine, or mixtures thereof.

5. A sensor in accordance with claim 1, wherein said fluorophore is selected from the group consisting of Patman, Laurdan, and Prodan.

6. A sensor in accordance with claim 1, wherein said liposomes are separated from said medium by a membrane which is permeable to the analyte but which is impermeable to the lipid layer and the fluorophore.

7. A sensor in accordance with claim 6, wherein said membrane comprises polytetrafluoroethylene.

8. A probe for use in the determination of the presence or amount of a lipid-soluble analyte in a medium, which comprises:
   a sensor comprising a lipid layer capable of dissolving the analyte, the lipid layer having a first phase condition in the absence of the analyte and a second phase condition, different from the first phase condition, in the presence of the analyte, said dissolving causing a phase change of the lipid layer from the first phase condition to the second phase condition in proportion to the amount of the analyte dissolved therein, and a fluorophore contained in the lipid layer, the fluorophore having a fluorescence characteristic that varies in response to the phase change of the lipid layer from the first phase condition to the second phase condition, wherein said lipid layer is in the form of liposomes immobilized on a porous fiber or in a hydrogel; and optical transmission means connected to said sensor.

9. A probe according to claim 8, wherein said optical transmission means is a single optical fiber.

10. A probe according to claim 8, wherein said optical transmission means is a plurality of optical fibers.

11. A probe according to claim 8, wherein said liposomes are immobilized in a hydrogel which comprises polyacrylamide, agarose, or gelatin.

12. A probe according to claim 8, wherein said fluorophore is Laurdan.

13. A system for use in the determination of the presence or amount of a lipid-soluble analyte in a medium, which comprises:
   a sensor comprising a lipid layer capable of dissolving the analyte, the lipid layer having a first phase condition in the absence of the analyte and a second phase condition, different from the first phase condition, in the presence of the analyte, said dissolving causing a phase change of the lipid layer from the first phase condition to the second phase condition in proportion to the amount of the analyte dissolved therein, and a fluorophore contained in the lipid layer, the fluorophore having a fluorescence characteristic that varies in response to the phase change of the lipid member from the first phase condition to the second phase condition, wherein said lipid layer is in the form of liposomes immobilized on a porous fiber or in a hydrogel;
   optical transmission means connected to said sensor;
   fluorescent radiation source means connected to said optical transmission means; and,
   measuring means connected to said optical transmission means for measuring the fluorescence characteristic of said fluorophore.

14. A system according to claim 13, wherein said transmission means is a plurality of optical fibers.

15. A system according to claim 13, which further comprises a reference sensor that is identical to said sensor except that said reference sensor further comprises a membrane separating the lipid layer from the medium, wherein said membrane is impermeable to the analyte, said reference sensor being connected by optical transmission means to said fluorescence radiation source means and said measuring means.

16. A system according to claim 13, wherein said liposomes are immobilized in a hydrogel which comprises polyacrylamide, agarose, or gelatin.

17. A system according to claim 13, wherein said fluorophore is Laurdan.

18. A system according to claim 13, wherein said measuring means is capable of comparing fluorescence at two different wavelengths, and said fluorophore undergoes a fluorescence wavelength shift when said lipid layer undergoes a phase change in the presence of said analyte.

19. A method for detecting a lipid-soluble analyte in a medium, which comprises contacting said medium with a sensor according to claim 1, and measuring a change in the fluorescence characteristic of the fluorophore.

20. A method in accordance with claim 19, wherein the fluorescence characteristic is the wavelength of maximum intensity of fluorescence emission by the fluorophore, the lifetime of a fluorescent excited state of the fluorophore, or a combination thereof.

21. A method in accordance with claim 19, wherein the lipid-soluble analyte is an anesthetic.

22. A method in accordance with claim 21, wherein the anesthetic is selected from the group consisting of isoflurane, halothane, enflurane, and ethanol.

23. A method in accordance with claim 19, wherein the medium is a tissue from an anesthetized patient or animal.

24. A method in accordance with claim 19, wherein said liposomes are immobilized in a hydrogel which comprises polyacrylamide, agarose, or gelatin.

25. A method in accordance with claim 19, wherein said liposomes comprise one or a mixture of $C_8$ to $C_{20}$ phospholipids.

26. A method in accordance with claim 25, wherein the phospholipids are selected from the group consisting of dipalmitoyl phosphatidylcholine, dimyristoyl phosphatidylcholine, and mixtures thereof.

27. A method in accordance with claim 19, wherein said fluorophore is selected from the group consisting of Patman, Laurdan, and Prodan.

28. A method in accordance with claim 19, wherein an optical transmission means is connected to the sensor and said optical transmission means is at least one optical fiber.

29. A method in accordance with claim 19, wherein said liposomes are separated from said medium by a membrane which is permeable to the analyte but which is impermeable to said fluorophore.

30. A method in accordance with claim 29, wherein said membrane comprises polytetrafluoroethylene.

* * * * *